(12) United States Patent
Yamasoto et al.

(10) Patent No.: US 6,991,095 B1
(45) Date of Patent: Jan. 31, 2006

(54) PACKAGING BAG FOR PLASTER AND PACKAGED PLASTER

(75) Inventors: Shinji Yamasoto, Tosu (JP); Yasuhiro Ikeura, Tosu (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 10/019,400

(22) PCT Filed: Jun. 30, 2000

(86) PCT No.: PCT/JP00/04352

§ 371 (c)(1),
(2), (4) Date: Dec. 28, 2001

(87) PCT Pub. No.: WO01/02267

PCT Pub. Date: Jan. 11, 2001

(30) Foreign Application Priority Data

Jul. 2, 1999 (JP) ................................. 11-189204

(51) Int. Cl.
| | |
|---|---|
| *A61B 17/06* | (2006.01) |
| *B65D 73/00* | (2006.01) |
| *B65D 85/84* | (2006.01) |
| *B65D 81/26* | (2006.01) |

(52) U.S. Cl. ...................... 206/204; 206/438; 206/484; 206/484.2; 206/524.2; 206/524.4

(58) Field of Classification Search ................ 206/438, 206/440, 484, 484.2, 37, 524.1, 524.2, 524.3, 206/524.4, 828, 204; 424/449, 448
See application file for complete search history.

(56) References Cited

U.S. PATENT DOCUMENTS

| | | | | |
|---|---|---|---|---|
| 4,657,133 A | * | 4/1987 | Komatsu et al. ............ | 206/204 |
| 4,861,632 A | * | 8/1989 | Caggiano .................... | 206/204 |
| 5,698,217 A | * | 12/1997 | Wilking ...................... | 424/448 |

FOREIGN PATENT DOCUMENTS

| | | |
|---|---|---|
| JP | S62-165264 | 10/1987 |
| JP | 03-109917 | 5/1991 |

(Continued)

OTHER PUBLICATIONS

Partial Translation of Japanese Laid Open Utility Model Application No. H-7-28550, Publication Date May 30, 1995. Translation of Paragraphs [0019] and [0020]. Reference supplied by applicant.*

(Continued)

*Primary Examiner*—David T. Fidei
*Assistant Examiner*—J. Gregory Pickett
(74) *Attorney, Agent, or Firm*—Fitch Even Tabin & Flannery (57) ABSTRACT

Packaged patch (10) according to the invention comprises patch (2) situated in space (4) inside patch package (3) composed of laminated packaging material (1), and its edges are sealed. Laminated packaging material (1) comprises hygroscopic material layer (13) made of LDPE containing 20–40 wt % of an inorganic filler, situated between moisture-permeable material layer (14) made of LDPE and having a moisture permeability of 40–120 $g/m^2$/day and a screen material layer which blocks penetration of moisture, etc. and is composed of HDPE layer (12) and aluminum foil (11). The saturation hygroscopicity of laminated packaging material (1) is 2–30 $g/m^2$ under atmosphere conditions with a temperature of 25° C. and a relative humidity of 75%. This construction sufficiently reduces the effect of moisture on a drug in patch (2) and allows patch (2) to be held in a stable state for prolonged periods, while also improving the economy and handleability of patch package (3).

15 Claims, 1 Drawing Sheet

FOREIGN PATENT DOCUMENTS

| | | |
|---|---|---|
| JP | 04-189779 | 7/1992 |
| JP | 04-189779 A | 7/1992 |
| JP | 05-039379 | 2/1993 |
| JP | 05-039379 A | 2/1993 |
| JP | 06-209981 A | 8/1994 |
| JP | 07-28550 | 5/1995 |
| JP | 7-28550 A | 5/1995 |
| JP | 08-040910 A | 2/1996 |
| JP | 08-325141 | 12/1996 |
| JP | 08-325141 A | 12/1996 |
| JP | 09-122221 | 5/1997 |
| JP | 10-167284 | 6/1998 |

OTHER PUBLICATIONS

"Packaging Technology Manual", Aggregate Corporation of Nippon Packaging Technology Associate, 1" Ed., pp. 388-389, Jul. 1, 1995.

English translation of third party reference cited in JP H11-189204.

* cited by examiner

Fig.1

PACKAGING BAG FOR PLASTER AND PACKAGED PLASTER

This application is the National phase of International Application PCT/JP00/04352, filed 30 Jun. 2000, which designated the U.S. and that International Application was not published under PCT Article 21(2) in English.

TECHNICAL FIELD

The present invention relates to a patch package and to a packaged patch.

BACKGROUND ART

It may be generally stated that when a patch having a drug effect is attached to skin or the like, the drug serving as the active ingredient of the patch is released, passes through the skin and permeates to the blood, thereby exhibiting satisfactory bioefficacy in the body. In order to maintain a stable concentration of the drug in the blood to increase its bioavailability, the releasability of the drug from the patch must be favorably maintained. For this purpose, it is important to avoid impairment of the drug release property of the patch during the period lasting from preparation of the patch to the moment of its use.

The drug will usually be included in the adhesive of the patch, and thus if the patch is allowed to stand in air the solubility of the drug in the adhesive substance is reduced, tending to cause separation of the drug by crystallization. This results in the problem of a lower drug release rate from the adhesive layer.

Techniques for preventing a lower drug release rate include those disclosed in Japanese Unexamined Patent Publication HEI No. 8-40910, Japanese Unexamined Patent Publication HEI No. 8-325141 and elsewhere, based on such concepts as patch manufacturing environment humidity control, nitrogen substitution and packaging of desiccants with patches. Also, Japanese Unexamined Patent Publication HEI No. 5-39379 discloses a humidity-controlling shaped article containing magnesium sulfate.

DISCLOSURE OF THE INVENTION

The present inventors conducted a detailed study of the prior art, and as a result discovered the existence of certain problems. Specifically, humidity control or nitrogen substitution of the manufacturing environment requires greater investment in manufacturing equipment or an increased scale and number of manufacturing steps, thus leading to higher costs. Using a desiccant package poses the problem of increased product bulkiness, while users also run the risk of accidental ingestion of the desiccant. In addition to these economical and handling issues, conventional humidity-controlling shaped articles have tended to not always provide a sufficient humidity-controlling effect for drug-containing patches.

It is therefore an object of the present invention, which has been accomplished in light of these circumstances, to provide a patch package which can adequately alleviate the effect of moisture on a drug contained in the patch in order to maintain long-term stability of the patch, and which is also superior in terms of economy and handleability. It is another object of the invention to provide a packaged patch that can satisfactorily maintain the release properties of the drug from the patch.

The present inventors have conducted much diligent research aimed at achieving these objects, and have succeeded in completing the present invention upon finding that the type and properties of the packaging material has a governing effect on the releasability of the drug from a patch.

In light of this finding, the patch package according to the invention is therefore characterized by comprising a laminated packaging material with a saturation hygroscopicity of 2–30 g/m$^2$ under atmosphere conditions with a temperature of 25° C. and a relative humidity of 75%, wherein a hygroscopic material layer composed of a first resin containing 20–40 wt % of an inorganic filler is situated between a moisture-permeable material layer composed of a second resin and having a moisture permeability of 40–120 g/m$^2$/day and a screen material layer which blocks penetration of moisture and light, and by being shaped into a pouch with the moisture-permeable material layer on the inside.

In the patch package constructed in this manner, water vapor, or water molecules, in the air contained inside the shaped pouch gradually permeate the moisture-permeable material layer on the innermost side, reaching the hygroscopic material layer. Some of these water molecules are absorbed into the inorganic filler contained in the hygroscopic material layer. There are also water molecules that pass through the hygroscopic material layer and diffuse out of it, and some of these water molecules are blocked by the screen material layer and return to the hygroscopic material layer, where they are either absorbed into the inorganic filler or in many cases may pass through the hygroscopic material layer and moisture-permeable material layer in the opposite direction, being returned to the interior space of the patch package.

Although this behavior of the water molecules has been explained in simple terms for convenience, in actuality it is thought that the water molecules behave in a more complex manner due to water molecule diffusion and absorption/desorption equilibrium by the inorganic filler, etc., and the function is not limited to this explanation.

When the moisture permeability of the moisture-permeable material layer and the inorganic filler content of the hygroscopic material layer are within the aforementioned ranges, the saturation hygroscopicity of the laminated packaging material is kept within 2–30 g/m$^2$ under atmosphere conditions with a temperature of 25° C. and a relative humidity of 75%. If the saturation hygroscopicity of the laminated packaging material is less than 2 g/m$^2$, the moisture present in the interior space of the patch package will not be sufficiently absorbed into the laminated packaging material, and therefore when a patch is accommodated in the patch package, the drug in the patch will tend to easily separate out.

On the other hand, if the saturation hygroscopicity of the laminated packaging material is greater than 30 g/m$^2$, the moisture present in the interior space may be absorbed into the laminated packaging material to an extent creating an unsuitably dry state in the patch. When a patch is accommodated therein, this will lead to evaporation of the adhesive component and volatile components in the patch, tending to lower the adhesive strength. The patch package of the invention therefore satisfactorily maintains the humidity in the interior space within a range suitable for a patch. Thus, when a patch is accommodated in the patch package, it is possible to adequately prevent separation of the drug in the patch without risking impairment of the adhesive strength of the patch.

The inorganic filler used as the hygroscopic material has high hygroscopicity and excellent dispersability in resins, thus allowing a reduction in the amount (weight, volume) of hygroscopic material required for use and permitting a thinner laminated packaging material to be achieved. The first resin and second resin may be either the same or different.

The first resin and second resin are preferably low-density polyethylene, and the screen material layer preferably comprises a metal foil and a high-density polyethylene layer. Low-density polyethylene (hereunder abbreviated to "LDPE") has a less compact molecular structure than high-density resins such as high-density polyethylene (hereunder abbreviated to "HDPE"), and more excellent moisture permeability. The LDPE component therefore provides the hygroscopic material layer and the moisture-permeable material layer with a suitable degree of moisture permeability. As a result, the moisture permeability of the moisture-permeable material layer can be reliably maintained to a value within the aforementioned range. The water molecules passing through the moisture-permeable material layer and reaching the hygroscopic material layer thus easily penetrate into the layers and are reliably absorbed into the inorganic filler. Constructing the screen material layer of a metal foil and an HDPE layer can further increase the moisture and light blocking property.

Preferably, the thickness of the hygroscopic material layer is 20–40 μm, the thickness of the moisture-permeable material layer is 5–15 μm, the thickness of the high-density polyethylene layer composing the screen material layer is 10–30 μm and the thickness of the metal foil composing the screen material layer is 5–15 μm.

This will allow saturation hygroscopicity in the range mentioned above to be reliably and satisfactorily achieved for the laminated packaging material. Also, since the total thickness of the laminated packaging material will be no greater than about 100 μm, it will not be bulky even when a patch is accommodated therein. Thus, when a patch is placed inside the patch package to prepare a packaged patch (product), the holding density or storage density in the outer box or outer bag of the final product may be increased, thus allowing a reduction in space to be achieved.

The patch package of the invention is then sealed by heat sealing of the laminated packaging material, with a suitable heat seal strength being from 1.0 kg/25 mm to 5.0 kg/25 mm.

This will provide a very firm seal for the patch package, to adequately prevent penetration of moisture from the outside into the interior of the patch package. When each layer of the laminated packaging material composing the patch package is formed primarily of a thermoplastic resin such as LDPE or HDPE, utilizing a heat seal will result in a very simple and firm seal. If the heat seal strength is less than 1.0 kg/25 mm, the seal may be affected by the surrounding environment during storage so that the seal portion may tend to easily peel open. On the other hand, if the heat seal strength is greater than 5.0 kg/25 mm, manufacturing defects may occur, such as breakage of the seal section during the heat sealing.

The packaged patch of the invention is characterized in that a patch having a support and a pressure-sensitive adhesive composed mainly of a styrene-isoprene-styrene block copolymer laminated on the support is situated in a patch package according to the invention, with the condition that the total surface area of the interior of the patch package is 1.2–10 times the total surface area of the patch.

The patch package of the invention can produce a humidity environment that is highly suited for holding of patches containing such pressure-sensitive adhesives. A patch with a pressure-sensitive adhesive can therefore be more satisfactorily held for longer periods of time.

Furthermore, since the total thickness of the laminated packaging material forming the packaged patch can be very small, as mentioned above, the thickness of the packaged patch can be very close to the thickness of the patch itself. Consequently, the packaged patch will not be bulky and the holding density or storage density in the outer box or outer bag of the final product may be increased, thus allowing a reduction in space to be achieved. Also, if the total surface area of the interior of the patch package is 1.2–10 times the effective area of the patch, the patch may be stored for long periods in a satisfactorily humidity-controlled environment. The handleability of the patch for insertion and removal from the patch package is also improved.

The "moisture permeability" according to the present invention is the value calculated from the relationship represented by the following formula (1):

$$\eta = 240 \times m/t/S \tag{1}$$

where the measurement is carried out using a permeation cell containing anhydrous calcium chloride sealed with a moisture-permeable material (moisture-permeable area: 28.274 cm$^2$) and kept at an external temperature of 40° C. and a relative humidity of 90%, and this condition is maintained for one day to a few days, according to the water vapor permeability test specified by the Japan Industrial Standards (JIS) Z0208 (1976). In the formula, η is the moisture permeability (g/m$^2$/day), S is the moisture-permeable area (cm$^2$), t is the time period (hr) of the measurement and m is the mass increase (mg) during the measurement (during time t (hr)).

The "saturation hygroscopicity" according to the invention is the saturation moisture absorption after the film-like laminated packaging material has been allowed to stand for a few days to a few weeks in a sealed space kept at a temperature of 25° C. and a relative humidity of 75%, and it is the value calculated from the relationship represented by the following formula (2):

$$\epsilon = As/Ss \tag{2}$$

In this formula, ε is the saturation hygroscopicity (g/m$^2$), As is the saturation moisture absorption amount (g) and Ss is the area of the laminated packaging material (m$^2$).

The "low density polyethylene" (LDPE) according to the invention is polyethylene with a specific gravity satisfying the relationship represented by the following inequality (3):

$$0.91 \leq \rho < 0.94 \tag{3}$$

In this inequality, ρ is the specific gravity of the polyethylene (g/cm$^3$) (same hereunder).

The "high density polyethylene" (HDPE) according to the invention is polyethylene with a specific gravity satisfying the relationship represented by the following inequality (4):

$$0.94 \leq \rho < 0.96 \tag{4}$$

The "heat seal strength" according to the invention is determined using a test strip of the laminated packaging material having a width of 25 mm and a length of 80 mm, based on tensile strength and elongation as specified by the Japan Industrial Standards (JIS) Z0237 (1991.6), and it is the value of the force required for pulling to a test length of 50 mm at a pull rate of 50 mm/min using a tensile tester a specified by the Japan Industrial Standards (JIS) Z0237 (1991.6.2).

The "effective area" of the patch according to the invention is the area of the site from which the drug contained in the patch is principally released. A patch generally consists of a drug-containing pressure-sensitive adhesive applied onto a support, and since the drug is principally released from the side of the pressure-sensitive adhesive that is not in contact with the support, the area of this side in this case would constitute the "effective area".

BEST MODE FOR CARRYING OUT THE INVENTION

An embodiment of the invention will now be explained with reference to the attached drawing.

Figure 1:
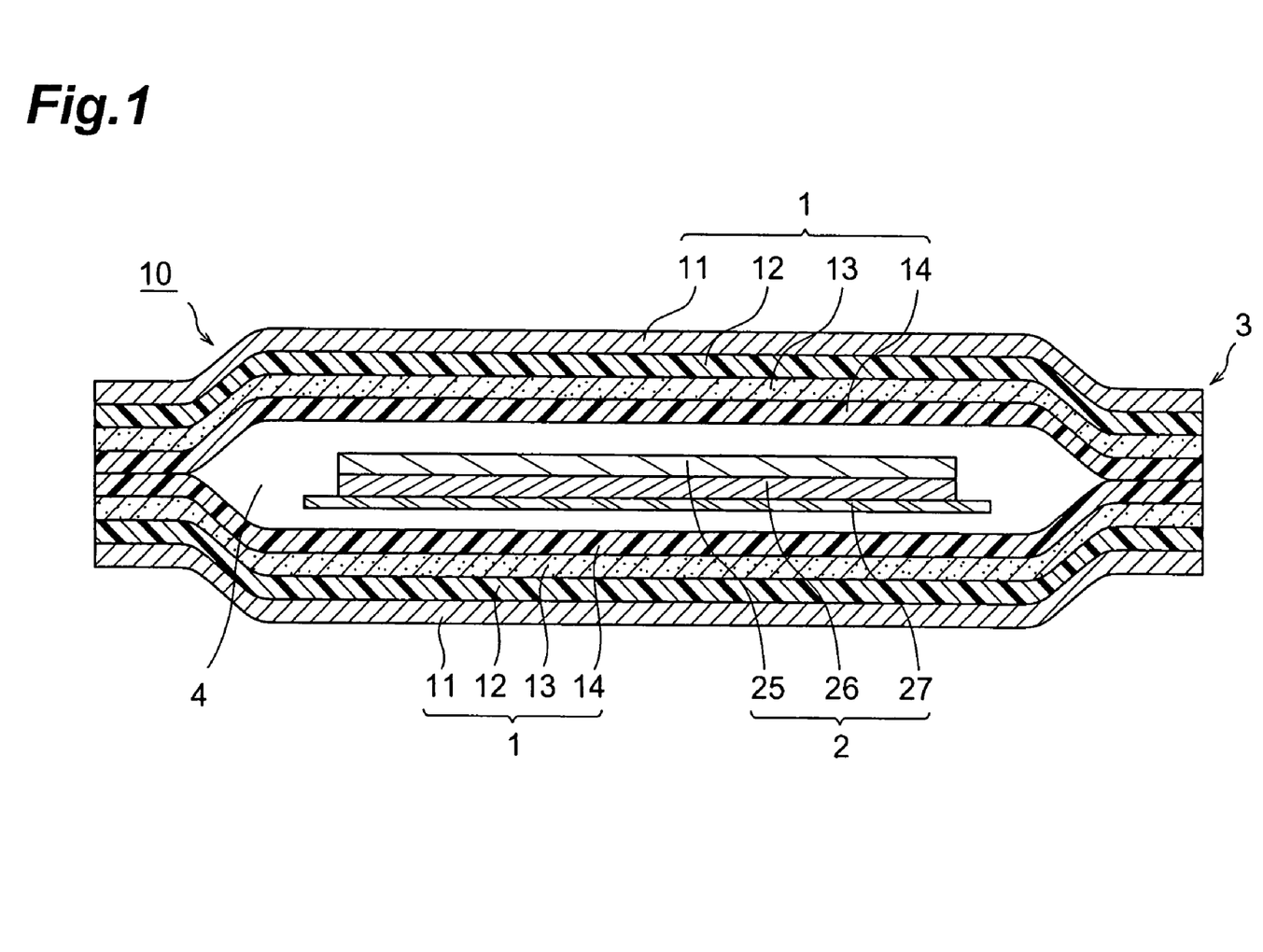
FIG. 1 is a cross-sectional schematic view of a preferred embodiment of a packaged patch according to the invention.

FIG. 1 is a cross-sectional schematic view of a preferred embodiment of a packaged patch according to the invention. As seen in FIG. 1, the packaged patch 10 comprises a patch 2 situated in the space 4 inside a pouch-like patch package 3 composed of a laminated packaging material 1. The edges of the patch package 3 are (hermetically) sealed. The patch package 3 and the patch 2 will be explained in detail separately.

(Patch package)

The laminated packaging material 1 composing the patch package 3 is prepared by laminating a moisture-permeable material layer 14 composed of an LDPE (second resin), a hygroscopic material layer 13 composed of an inorganic filler dispersed in an LDPE (first resin) and a screen material layer composed of an HDPE layer 12 and an aluminum foil 11, in that order from the inside, and these are attached to each other.

According to this embodiment, the thicknesses of the aluminum foil 11, HDPE layer 12, hygroscopic material layer 13 and moisture-permeable material layer 14 are preferably 5–15 $\mu$m, 10–30 $\mu$m, 20–40 $\mu$m and 5–15 $\mu$m, respectively. The thickness of the laminated packaging material 1 is preferably 40–100 $\mu$m.

The saturation hygroscopicity of the laminated packaging material 1 is 2–30 g/m$^2$ under atmosphere conditions with a temperature of 25° C. and a relative humidity of 75%. If the saturation hygroscopicity is less than 2 g/m$^2$, the moisture (water vapor, water molecules) contained in the air in the space 4 will not be sufficiently absorbed into the laminated packaging material 1, so that the drug in the patch 2 will tend to more easily separate out.

On the other hand, if the saturation hygroscopicity is greater than 30 g/m$^2$, the moisture in the space 4 may be absorbed into the laminated packaging material to an extent creating an unsuitably dry state in the patch 2, leading to easier evaporation of the adhesive component and volatile components in the patch. This tends to result in a reduced adhesive property of the patch 2.

In order to achieve this saturation hygroscopicity for the laminated packaging material 1, the moisture-permeable material layer 14 composing the laminated packaging material 1 is designed for a moisture permeability of 40–120 g/m$^2$/day. As mentioned above, the moisture-permeable material layer 14 is composed of LDPE. LDPE has superior moisture permeability compared to high-density resins such as HDPE, and can therefore reliably exhibit moisture permeability within the range specified above.

In order to achieve this moisture permeability with HDPE or the like, the layer thickness must be extremely small. The strength of the moisture-permeable material layer is therefore reduced to a level which is poorly able to withstand practical use. However, since it is possible to guarantee a suitable thickness for the moisture-permeable material layer 14 according to the invention, the strength of the moisture-permeable material layer 14 may be of a satisfactory level for practical use.

If the moisture permeability of the moisture-permeable material layer 14 is less than 40 g/m$^2$/day, the moisture contained in the air in the space 4 may be unable to adequately reach the hygroscopic material layer 13. On the other hand, if the moisture permeability is greater than 120 g/m$^2$/day, the interior of the space 4 will tend to be dried to an extent unsuitable for holding of the patch 2. In either case, it will tend to be difficult to maintain adjustment of the saturation hygroscopicity of the laminated packaging material 1 to within the aforementioned range, i.e., 2–30 g/m$^2$.

In order to achieve this saturation hygroscopicity for the laminated packaging material 1, the content (proportion) of the inorganic filler dispersed in the hygroscopic material layer 13 composing the laminated packaging material 1 is specified as 20–40 wt % of the total of the hygroscopic material layer 13. The hygroscopic material layer 13 employs LDPE as the matrix because of its excellent dispersability for inorganic fillers. The inorganic filler at the specified content can thus be uniformly dispersed in the hygroscopic material layer 13.

As mentioned above, LDPE has excellent moisture permeability and therefore moisture that has permeated the moisture-permeable material layer 14 easily penetrates into the hygroscopic material layer 13. As a result, the frequency of contact between the moisture and the inorganic filler in the hygroscopic material layer 13 is increased, thus promoting absorption of the moisture into the inorganic filler.

If the inorganic filler content of the hygroscopic material layer 13 is less than 20 wt %, moisture that has permeated the moisture-permeable material layer 14 will tend not to be sufficiently absorbed into the hygroscopic material layer 13. On the other hand, the inorganic filler content preferably does not exceed 40 wt %, since the space 4 will tend to be dried to an extent unsuitable for holding of the patch 2, and the adhesive components and volatile components of the patch 2 may adsorb onto the hygroscopic material layer 13. In either case, it will tend to be difficult to maintain adjustment of the saturation hygroscopicity of the laminated packaging material 1 to within the aforementioned range. If the inorganic filler content is greater than 40 wt %, it may also become difficult to guarantee a hermetic seal when sealing the laminated packaging material 1 with a heat seal.

The type and form of the inorganic filler are not particularly restricted, and for example, barium oxide, calcium chloride, magnesium sulfate, calcium oxide, calcium sulfate, lithium chloride, lithium perchlorate, alumina, silica gel or the like may be used. Magnesium sulfate is preferred for use among these because it has a humidity-controlling property suitable for the patch 2 and also has excellent handleability. Magnesium sulfate is often used in the form of a hydrate, in which case its hydrate number is preferably small from the standpoint of the moisture-absorbing function of the patch package 3.

(Patch)

The patch 2 comprises a drug-containing pressure-sensitive adhesive 26 laminated on a support 25, with a liner 27 attached thereto. The material of the support 25 is not particularly restricted, but is preferably one with excellent flexibility while maintaining a satisfactory drug release property. As such materials there may be mentioned stretchable or non-stretchable films made of resins such as polyester, polypropylene, polyethylene, vinyl acetate, vinyl chloride and the like, woven fabrics or nonwoven fabrics made of fibers of such resins, or composites of such films and woven or nonwoven fabrics.

The pressure-sensitive adhesive 26 comprises at least a base, a tackifier and a softening agent, and although the composition is not particularly restricted, it is preferably one which is safe for the skin and has excellent adhesion onto skin; in most cases it may be one which is conventionally used for patches.

As bases there may be mentioned, for example, natural rubber, synthetic rubber, acrylic, silicone types, and synthetic rubber polymers such as polyisobutylene or polyisoprene, which may be used either alone or in combinations of two or more. Styrene-isoprene-styrene block copolymer (hereunder referred to as "SIS") is preferred among the specific compounds belonging to this group from the standpoint of drug release property and safety for the skin.

As tackifiers there may be mentioned alicyclic saturated hydrocarbon resins, polyterpene resins, petroleum resins, rosins, hydrogenated rosins, hydrogenated rosin esters, oil-soluble phenol resins and the like. Alicyclic saturated hydrocarbon resins and hydrogenated rosin esters are particularly preferred among these.

The softening agent is not particularly restricted so long as it is one capable of plasticizing and softening the base such as SIS and the tackifier such as a rosin ester derivative, and maintaining suitable adhesion on the skin. Specific examples which may be used include almond oil, olive oil, camellia oil, persic oil, peanut oil, olefinic acid, liquid paraffin and the like, among which liquid paraffin is particularly preferred for use because of its highly superior adhesion onto skin.

The drug to be included in the pressure-sensitive adhesive 26 is not particularly restricted, and for example, there may be used antiemetics such as granisetron hydrochloride, azasetron hydrochloride, ondansetron hydrochloride and ramosetron hydrochloride; polakisuria treatments such as oxybutynin hydrochloride; Ca antagonists such as nifedipine, nisoldipine, nicardipine and nitredipine; corticosteroids such as hydrocortisone, prednisolone and clobetasol propionate; anti-inflammatory analgesics such as indomethacin, ketoprofen, flurbiprofen, felbinac, ketorolac and diclofenac sodium; hypnotic analgesics such as phenobarbital, triazolam, nitrazepam and lorazepam; neuroleptics such as fluphenazine, diazepam and chlorpromazine; antihypertensive agents such as clonidine, clomipramine hydrochloride, clonidine hydrochloride, pindolol, propranolol, nitrendipine and metoprolol; hypotensive diuretics such as hydrothiazide; antibiotics such as penicillin, tetracycline, erythromycin and chloramphenicol; anesthetics such as lidocaine, dibucaine hydrochloride, tetracaine and ethyl aminobenzoate; antibacterial agents such as benzalkonium hydrochloride and clotrimazole; vitamins such as vitamin A; antiepileptics such as nitrazepam; coronary vasodilators such as nitroglycerin and isosorbide dinitrate; antihistamines such as diphenhydramine and chlorpheniramine; antitussives such as tulobuterol hydrochloride, salbutamol, ketotifen fumarate, tranilast and isoproteronol hydrochloride; antidepressants such as doxepin; cerebral circulation ameliorants such as hydergine, dihydroergotoxine mesylate and ifenpradil; anticancer agents such as 5-fluorouracil; muscle relaxants such as eperisone and dantrolene; analgesics such as fentanyl and morphine; hormones such as estradiol, progesterone and LH-RH; immunoregulators such as polysaccharides, auranofin and lobenzarit; choleretic agents such as ursodesoxycholic acid; diuretics such as hydroflumethiazide; smoking cessation aids such as nicotine; agents for diabetes such as tolbutamide; gout treatment agents such as colchicine; antiparkinson agents such as amantadine and levodopa; antivertigo agents such as difenidol and betahistine; and antispasmodics such as atropine and scopolamine. These drugs may be used alone, or in combinations (mixtures) of two or more depending on the need so long as no undesirable interactions are produced.

As drugs that are particularly useful when applying the patch package 3 of the invention there may be mentioned eperisone, estradiol and its derivatives, dantrolene, diclofenac sodium and scopolamine. "Estradiol and its derivatives" refers to natural estrogen, synthetic estrogen and their derivatives, among which there may be mentioned, for example, estradiol, estradiol benzoate, estradiol dipropionate, estradiol valerate and ethynyl estradiol.

As explained above, various formulations may be selected as the pressure-sensitive adhesive 26 in the patch 2, and one containing SIS as the base is particularly preferred from the standpoint of preventing skin eruption and excessive irritation (adequate safety on the skin), preventing peeling after attachment (adequate adhesion), drug absorption and retention, a suitable drug release property, and allowing maximum utilization of the hygroscopicity of the patch package 3.

The component composition of the pressure-sensitive adhesive 26 preferably includes the base at 10–74.1 wt % (when the base contains SIS and/or polyisobutylene, the SIS content is preferably 10–40 wt % and the polyisobutylene content is preferably 5–35 wt %. However, their total content must not exceed 74.1 wt %. Also these particular components need not be present.), the tackifier at 10–55 wt %, the softening agent at 15–30 wt % and the drug at 0.1–5 wt %.

The aforementioned preferred range for the base content can be determined based on the preferred ranges for the contents of the tackifier, softening agent and drug. The thickness of the pressure-sensitive adhesive 26 is preferably 10–300 $\mu$m.

The material for the liner 27 is not particularly restricted, and may be silicone or fluorine treated polyester film, paper or the like.

The method of producing the patch 2 having this manner of construction may involve, for example, [1] heating the base components to dissolution and then adding the drug, applying it onto the support, covering it with the liner and cutting it into the desired shape as a product, or [2] heating the base components to dissolution and then adding the drug, applying it onto a film that has been release treated, and contact bonding this onto an appropriate support to complete the product.

The method of producing the packaged patch 10 is not particularly restricted, and for example, the following method may be mentioned. Specifically, the method used may involve folding over the sheet-like (film-like) laminated packaging material 1 with the moisture-permeable material layer 14 on the inside so as to sandwich both sides of the patch 2, and then forming a seal by applying heat to the desired location with an ordinary sealer or the like (a "heat seal") and cutting out an outline on the seal section.

The heat seal strength is preferably 1.0 kg/25 mm to 5.0 kg/25 mm. If the heat seal strength is less than 1.0 kg/25 mm, the seal may be affected by the surrounding environment during storage so that the seal portion may tend to easily peel open. On the other hand, if the heat seal strength is greater than 5.0 kg/25 mm, manufacturing defects may occur, such as breakage of the seal section during the heat sealing.

In the packaged patch 10, the total surface area of the interior of the patch package 3 is specified as 1.2–10 times the total effective area of the patch 2. If this ratio is less than 1.2, the inorganic filler content will tend to be insufficient and it may not be possible to dry the space 4 in the packaged patch 10 to an extent allowing long-term storage of the patch in a satisfactory environment. This situation can also hamper removal of the patch 2 from the patch package 3.

On the other hand, if the ratio exceeds 10, the space 4 will tend to be dried to an excessive degree, and the adhesive components and volatile components of the patch 2 may adsorb onto the patch package 3. The aforementioned range for this ratio is even more preferred when using a patch such as explained above wherein the pressure-sensitive adhesive 26 is composed mainly of SIS.

In the embodiment described above, the screen material layer of the laminated packaging material 1 comprises an HDPE layer 12 and an aluminum foil 11, but the laminated packaging material 1 may be made of other materials so long as they are capable of blocking moisture and light, and it preferably has a heat sealable material such as the HDPE layer.

Examples of other materials include metal foils other than aluminum, on which there may be laminated one or more from among heat sealable polyethylene, polypropylene and ethylene-vinyl acetate. From the standpoint of the outer appearance, polyester, cellophane, paper or the like is preferably laminated on the outside of aluminum foil 11 or another type of metal foil.

If intended for use with a patch that does not require blockage of light of a certain wavelength, the patch package 3 may be formed of a material which is transparent to that wavelength of light, but from the standpoint of stably holding the patch components, it preferably blocks near infrared light, infrared light and ultraviolet light. Although LDPE is used here as the resin of the hygroscopic material layer 13, another resin may also be used, and preferably one with appropriate moisture permeability and heat sealability, as well as excellent dispersion properties for the inorganic filler. As such other resins there may be mentioned polypropylene and ethylene-vinyl acetate.

With the packaged patch 10 constructed in this manner and the patch package 3 composing it, water molecules present in the space 4 gradually permeate the moisture-permeable material layer 14 situated on the innermost side of the patch package 3. Some of these water molecules are absorbed into the inorganic filler contained in the hygroscopic material layer 13.

Some of the water molecules also diffuse through the hygroscopic material layer 13 to the HDPE layer 12 side, and most of these water molecules are blocked by the screen material layer made of the HDPE layer 12 and aluminum foil 11, return to the hygroscopic material layer 13, and are absorbed into the inorganic filler. A portion of these water molecules may instead pass through the hygroscopic material layer 13 and moisture-permeable material layer 14 in the opposite direction, returning again to the space 4. As a result, the humidity or water vapor pressure in the space 4 approaches an equilibrium which is governed by the volume of the space 4, the moisture permeability of the moisture-permeable material layer 14, etc.

Since the moisture-permeability of the moisture-permeable material layer 14 and the inorganic filler content of the hygroscopic material layer 13 are in the ranges specified above, the saturation hygroscopicity of the laminated packaging material 1 is satisfactorily kept between 2–30 g/m$^2$ under atmosphere conditions with a temperature of 25° C. and a relative humidity of 75%. As the saturation hygroscopicity of the laminated packaging material 1 is a value within this range, the humidity in the space 4 is satisfactorily maintained in a range suitable for the patch 2, so that separation of the drug in the patch 2 can be adequately prevented and the adhesive property of the patch is not impaired.

The effects of moisture on the drug in the patch 2 can therefore be sufficiently alleviated, allowing the patch 2 to be held in a stable state for long periods of time.

Because this effect is achieved without manufacturing environment humidity control, nitrogen substitution or packaging of a desiccant with the patch 2, it is also possible to achieve an adequate increase in economy and handleability. Also, since no desiccant is required, the packaged patch 10 is not bulky and can be downsized. This increases the storage density for the packaged patch 10, allowing a reduction in required storage space.

A highly hygroscopic inorganic filler is used as the hygroscopic material, and because of the excellent diffusion properties of the inorganic filler into the resin, the amount (weight, volume) of the hygroscopic material can be reduced to achieve a thinner laminated packaging material 1. This contributes to further downsizing of the packaged patch 10.

Furthermore, since relatively highly moisture-permeable LDPE is used as the first resin and second resin, the hygroscopic material layer 13 and moisture-permeable material layer 14 composed of the LDPE exhibit suitable moisture permeability. The moisture permeability of the moisture-permeable material layer 14 can therefore be reliably kept to a value within the range specified above. Hence, the water molecules that have passed through the moisture-permeable material layer 14 and reached the hygroscopic material layer 13 easily penetrate into the hygroscopic material layer 13, and are reliably absorbed into the inorganic filler. In addition, the screen material layer is formed of aluminum foil 11 and an HDPE layer 12, thus allowing enhanced moisture and light blockage.

Since the thickness of the hygroscopic material layer 13 is 20–40 μm, the thickness of the moisture-permeable material layer 14 is 5–15 μm, the thickness of the HDPE layer 12 of the screen material layer is 10–30 μm and the thickness of the aluminum foil 11 of the screen material layer is 5–15 μm, the saturation hygroscopicity of the laminated packaging material 1 is reliably and satisfactorily achieved within the range specified above. Also, limiting the total thickness of the laminated packaging material 1 to no greater than about 100 μm prevents bulkiness even when the patch is held therein. The holding density in the outer box or outer bag of the packaged patch 10 and the storage density may therefore be increased, thus allowing further reduction in space to be achieved.

When the heat seal strength of the laminated packaging material 1 is between 1.0 kg/25 mm to 5.0 kg/25 mm, a very firm seal is provided for the patch package 3, thus increasing the seal performance. This will adequately prevent penetration of moisture from the outside to the inside of the patch package 3. Also, since each layer of the laminated packaging material 1 composing the patch package 3 is formed primarily of a thermoplastic resin, a firm seal can very easily be created by heat sealing. A heat seal strength of greater than 1.0 kg/25 mm can prevent any tendency of the seal section to peel open during storage. A heat seal strength limited to no greater than 5.0 kg/25 mm can notably reduce manufacturing defects such as breakage of the seal section during heat sealing.

Since the patch package 3 provides a satisfactory degree of humidity suitable for a patch 2 containing a pressure-sensitive adhesive 26 composed mainly of SIS, a patch 2 comprising such a pressure-sensitive adhesive 26 can be satisfactorily held for longer periods of time. Also, if the total surface area of the interior of the patch package 3 is 1.2–10 times the effective area of the patch 2, the patch 2 may be stored for long periods in a satisfactorily humidity-controlled environment, while the handleability of the patch 2 for insertion and removal from the patch package 3 is also improved.

EXAMPLES

The present invention will now be explained in greater detail by way of examples, with the understanding that the invention is in no way limited to these examples.

Example 1

(1) Fabrication of patch package: Each of the following layers was laminated in order, and then the surface of the screen material layer was coated with cellophane (thickness: 20 μm) to fabricate a laminated packaging material.

Moisture-permeable material layer: LDPE (thickness: 10 μm, moisture permeability: 60 g/m²/day)

Hygroscopic material layer: LDPE (thickness: 30 μm, containing 30 wt % magnesium sulfate)

Screen material layer: HDPE (thickness: 20 μm), aluminum foil (thickness: 9 μm)

The hygroscopicity of the laminated packaging material was measured to be 23 g/m². This laminated packaging material was formed into a pouch with the moisture-permeable material layer on the inside and heat sealed to obtain a patch package.

(2) Fabrication of patch: The components of the following formulation were heated to dissolution and the resulting pressure-sensitive adhesive was applied onto a support and covered with a liner, after which it was cut to obtain an estradiol-containing patch with a single-side area (effective area) of 10 cm².

| | |
|---|---|
| SIS base: | 17.0 wt % |
| Polyisobutylene: | 14.9 wt % |
| Alicyclic saturated hydrocarbon resin: | 36.0 wt % |
| Liquid paraffin: | 30.0 wt % |
| Dibutylhydroxytoluene: | 0.1 wt % |
| Estradiol: | 2.0 wt % |

(3) Fabrication of packaged patch: The patch obtained in (2) was inserted into the patch package obtained in (1), and after further adding 1 μl of water into the patch package, it was sealed by heat sealing to obtain a packaged patch. The total surface area of the inside of the patch package was 15 cm².

Example 2

(1) Fabrication of patch package: Each of the following layers was laminated in order, and then the surface of the screen material layer was coated with cellophane (thickness: 20 μm) to fabricate a laminated packaging material.

Moisture-permeable material layer: LDPE (thickness: 5 μm, moisture permeability: 120 g/m²/day)

Hygroscopic material layer: LDPE (thickness: 30 μm, containing 38 wt % magnesium sulfate)

Screen material layer: HDPE (thickness: 30 μm), aluminum foil (thickness: 15 μm)

The hygroscopicity of the laminated packaging material was measured to be 30 g/m². This laminated packaging material was formed into a pouch with the moisture-permeable material layer on the inside and heat sealed to obtain a patch package.

(2) Fabrication of patch: The components of the following formulation were heated to dissolution and the resulting pressure-sensitive adhesive was applied onto a support and covered with a liner, after which it was cut to obtain a dantrolene-containing patch with a single-side area (effective area) of 10 cm².

| | |
|---|---|
| SIS base: | 20.0 wt % |
| Polyisobutylene: | 15.0 wt % |
| Alicyclic saturated hydrocarbon resin: | 26.0 wt % |
| Liquid paraffin: | 30.0 wt % |
| Crotamiton: | 8.0 wt % |
| Dantrolene: | 1.0 wt % |

(3) Fabrication of packaged patch: The patch obtained in (2) was inserted into the patch package obtained in (1), and after further adding 1 μl of water into the patch package, it was sealed by heat sealing to obtain a packaged patch. The total surface area of the inside of the patch package was 15 cm².

Example 3

(1) Fabrication of patch package: Each of the following layers was laminated in order, and then the surface of the screen material layer was coated with cellophane (thickness: 20 μm) to fabricate a laminated packaging material.

Moisture-permeable material layer: LDPE (thickness: 15 μm, moisture permeability: 40 g/m²/day)

Hygroscopic material layer: LDPE (thickness: 30 μm, containing 20 wt % magnesium sulfate)

Screen material layer: HDPE (thickness: 10 μm), aluminum foil (thickness: 5 μm)

The hygroscopicity of the laminated packaging material was measured to be 2 g/m². This laminated packaging material was formed into a pouch with the moisture-permeable material layer on the inside and heat sealed to obtain a patch package.

(2) Fabrication of patch: The components of the following formulation were heated to dissolution and the resulting pressure-sensitive adhesive was applied onto a support and covered with a liner, after which it was cut to obtain a diclofenac-containing patch with a single-side area (effective area) of 10 cm².

| | |
|---|---|
| SIS base: | 20.0 wt % |
| Polyisobutylene: | 6.0 wt % |
| Rosin ester: | 37.5 wt % |
| Liquid paraffin: | 29.5 wt % |
| Crotamiton: | 6.0 wt % |
| Diclofenac: | 1.0 wt % |

(3) Fabrication of packaged patch: The patch obtained in (2) was inserted into the patch package obtained in (1), and after further adding 1 μl of water into the patch package, it was sealed by heat sealing to obtain a packaged patch. The total surface area of the inside of the patch package was 12 cm$^2$.

Example 4

(1) Fabrication of patch package: Each of the following layers was laminated in order, and then the surface of the screen material layer was coated with cellophane (thickness: 20 μm) to fabricate a laminated packaging material.
Moisture-permeable material layer: LDPE (thickness: 10 μm, moisture permeability: 60 g/m$^2$/day)
Hygroscopic material layer: LDPE (thickness: 40 μm, containing 30 wt % magnesium sulfate)
Screen material layer: HDPE (thickness: 20 μm), aluminum foil (thickness: 9 μm)
The hygroscopicity of the laminated packaging material was measured to be 28 g/m$^2$. This laminated packaging material was formed into a pouch with the moisture-permeable material layer on the inside and heat sealed to obtain a patch package.

(2) Fabrication of patch: The components of the following formulation were heated to dissolution and the resulting pressure-sensitive adhesive was applied onto a support and covered with a liner, after which it was cut to obtain an estradiol-containing patch with a single-side area (effective area) of 10 cm$^2$.

| | |
|---|---|
| 2-ethylhexyl acrylate: | 95.4 wt % |
| Methacrylic acid: | 2.5 wt % |
| Polyethyleneglycol dimethacrylate: | 0.1 wt % |
| Benzoyl peroxide: | 1.0 wt % |
| Estradiol: | 1.0 wt % |

(3) Fabrication of packaged patch: The patch obtained in (2) was inserted into the patch package obtained in (1), and after further adding 1 μl of water into the patch package, it was sealed by heat sealing to obtain a packaged patch. The total surface area of the inside of the patch package was 15 cm$^2$.

Example 5

(1) Fabrication of patch package: Each of the following layers was laminated in order, and then the surface of the screen material layer was coated with cellophane (thickness: 20 μm) to fabricate a laminated packaging material.
Moisture-permeable material layer: LDPE (thickness: 10 μm, moisture permeability: 60 g/m$^2$/day)
Hygroscopic material layer: LDPE (thickness: 20 μm, containing 30 wt % magnesium sulfate)
Screen material layer: HDPE (thickness: 20 μm), aluminum foil (thickness: 9 μm)
The hygroscopicity of the laminated packaging material was measured to be 12 g/m$^2$. This laminated packaging material was formed into a pouch with the moisture-permeable material layer on the inside and heat sealed to obtain a patch package.

(2) Fabrication of packaged patch: An estradiol patch (area: 10 cm$^2$) fabricated in the same manner as Example 4 was inserted into the patch package obtained in (1), and after further adding 1 μl of water into the patch package, it was sealed (heat sealed) to obtain a packaged patch. The total surface area of the inside of the patch package was 15 cm$^2$.

Comparative Example 1

(1) Fabrication of patch package: Each of the following layers was laminated in order, and then the surface of the screen material layer was coated with cellophane (thickness: 20 μm) to fabricate a laminated packaging material.
Polyethylene laminate (thickness: 40 μm)
Aluminum foil (thickness: 9 μm)
The hygroscopicity of the laminated packaging material was measured to be 0.8 g/m$^2$. This laminated packaging material was formed into a pouch with the moisture-permeable material layer on the inside and heat sealed to obtain a patch package.

(2) Fabrication of packaged patch: An estradiol patch (area: 10 cm$^2$) fabricated in the same manner as Example 1 was inserted into the patch package obtained in (1), and after further adding 1 μl of water into the patch package, it was sealed (heat sealed) to obtain a packaged patch. The total surface area of the inside of the patch package was 15 cm$^2$.

Comparative Example 2

(1) Fabrication of patch package: Each of the following layers was laminated in order, and then the surface of the screen material layer was coated with cellophane (thickness: 20 μm) to fabricate a laminated packaging material.
Moisture-permeable material layer: LDPE (thickness: 20 μm, moisture permeability: 30 g/m$^2$/day)
Hygroscopic material layer: LDPE (thickness: 5 μm, containing 15 wt % magnesium sulfate)
Screen material layer: HDPE (thickness: 20 μm), aluminum foil (thickness: 9 μm)
The hygroscopicity of the laminated packaging material was measured to be 1.5 g/m$^2$. This laminated packaging material was formed into a pouch with the moisture-permeable material layer on the inside and heat sealed to obtain a patch package.

(2) Fabrication of packaged patch: A dantrolene patch (area: 10 cm$^2$) fabricated in the same manner as Example 2 was inserted into the patch package obtained in (1), and after further adding 1 μl of water into the patch package, it was sealed (heat sealed) to obtain a packaged patch. The total surface area of the inside of the patch package was 15 cm$^2$.

Comparative Example 3

For Comparative Example 3, a patch package according to the invention was fabricated as described in (1) below, and a packaged patch was fabricated as described in (2) in such a manner that the total surface area inside the patch package was 1.1 times the effective area of the patch.

(1) Fabrication of patch package: Each of the following layers was laminated in order, and then the surface of the screen material layer was coated with cellophane (thickness: 20 μm) to fabricate a laminated packaging material.
Moisture-permeable material layer: LDPE (thickness: 15 μm, moisture permeability: 40 g/m$^2$/day)
Hygroscopic material layer: LDPE (thickness: 30 μm, containing 20 wt % magnesium sulfate)
Screen material layer: HDPE (thickness: 10 μm), aluminum foil (thickness: 9 μm)
The hygroscopicity of the laminated packaging material was measured to be 2 g/m$^2$. This laminated packaging material was formed into a pouch with the moisture-permeable material layer on the inside and heat sealed to obtain a patch package.

(2) Fabrication of packaged patch: A dantrolene patch (area: 10 cm$^2$) fabricated in the same manner as Example 2 was inserted into the patch package obtained in (1), and after further adding 1 μl of water into the patch package, it was sealed (heat sealed) to obtain a packaged patch. The total surface area of the inside of the patch package was 11 cm$^2$.

(Release Test 1)

[Test sample]: Each of the patches fabricated in Examples 1–6 and Comparative Examples 1–3, immediately after fabrication (that is, with no storage period) and each of the packaged patches fabricated in Examples 1–6 and Comparative Examples 1–3 were stored in a thermo-hygrostatic bath at a temperature of 40° C. and a relative humidity of 75%, and the patches removed from the patch packages after 1 month, 3 months and 6 months were used as test samples.

[Test method]: The support side of the test sample was affixed to the center of a rotating cylinder using a silicone adhesive, and the liner was peeled off. Next, 900 ml of deaired water was placed in a container as the test liquid, the water (liquid) temperature was kept at 32±0.5° C., the rotating cylinder was immersed into the test liquid with a distance of 12±2 mm between the bottom end of the rotating cylinder and the bottom inside of the container, and the support of the rotating cylinder was anchored. The drug was allowed to elute into the test liquid while the rotating cylinder rotated at a rate of 50 rpm.

After 3 hours had passed from the start of the test (start of elution), 10 ml of the test liquid was taken at a location at the height were the patch was affixed and at least 10 mm from the container wall, and this was used as the sample solution. After taking the sample solution, the test liquid was replenished by immediately adding 10 ml of water preheated to 32±0.5° C.

Separately, approximately 0.02 g of each of the drugs in each patch was precisely measured out and ethanol (99.5%) was added for dissolution to 50 ml, after which 5 ml of this solution was measured out and water was added to 100 ml. After then measuring out 2 ml of this solution, water was added to 50 ml to prepare a dilution as the standard solution of known concentration.

The amounts of drug in 50 μl of the sample solution and this standard solution were determined by liquid chromatography, the drug concentration in the sample solution was quantified by comparison of the peak area (intensity) for each chart, and the amount of drug released from the patch of each sample was determined based on the concentration value, the dilution ratio of the sample solution and the solution volume. The results were used to calculate the release rate (%) of the drug based on the relationship represented by the following formula (5):

$$R_i = n_i/n_0 \times 100 \quad (5)$$

In this formula, $R_i$ represents the release rate (%) of the drug for a sample$_i$ (where i indicates whether the storage period of the patch in the patch package was 1 month, 3 months or 6 months), $n_i$ represents the amount of drug (mg) released from the sample$_i$ and no represents the amount of drug (mg) in the sample at a storage period of 0 months. The release rates calculated in this manner are summarized in Table 1.

TABLE 1

| | Release rate (%) | | | |
| --- | --- | --- | --- | --- |
| | Initial | 1 month | 3 months | 6 months |
| Example 1 | 18.7 | 17.8 | 18.1 | 18.2 |
| Example 2 | 18.7 | 18.6 | 18.7 | 18.5 |
| Example 3 | 18.7 | 18.4 | 17.9 | 18.3 |
| Example 4 | 27.2 | 26.8 | 27.1 | 26.7 |
| Example 5 | 27.2 | 24.4 | 23.5 | 23.9 |
| Comp. Ex. 1 | 18.7 | 9.8 | 6.5 | 4.9 |
| Comp. Ex. 2 | 18.7 | 15.9 | 13.1 | 10.7 |
| Comp. Ex. 3 | 18.7 | 16.5 | 15.2 | 13.9 |

As seen from Table 1, the packaged patches using patch packages according to the invention (Examples 1–5) had very low reduction in the release rate even after storage for 1–6 months. In contrast, Comparative Example 1 which employed a patch package with no organic filler-containing hygroscopic material layer and Comparative Example 2 which employed a patch package with a low magnesium sulfate content and low saturation hygroscopicity both had considerable reduction in the release rate after storage. This confirmed that the patch packages and packaged patches according to the invention are highly useful for satisfactorily and stably maintaining the release rates of drugs from patches.

Comparative Example 3, which had a total surface area inside the patch package that was 1.1 times the effective area of the patch, satisfactorily maintained the release rate compared to Comparative Examples 1 and 2, presumably due to the effect of the patch package of the invention. However, the reduction in the release rate of Comparative Example 3 was much larger than Examples 1 to 5. This also demonstrates the effectiveness of the packaged patch of the invention.

(Storage test)

The laminated packaging material obtained in Example 1 was used for shaping into pouches with the heat seal strengths listed as (1) to (3) below to obtain patch packages (100 each), and these were allowed to stand for 1–12 months under atmosphere conditions with a temperature of 60° C. and a relative humidity of 75%.

0.8 kg/25 mm
1.0 kg/25 mm
2.5 kg/25 mm

As a result of constant observation of the "peeling" of the heat seal sections of the packages during the storage period, the patch packages prepared with heat seal strengths of 1.0 kg/25 mm and 2.5 kg/25 mm exhibited absolutely no "peeling". In contrast, the patch packages prepared with a heat seal strength of 0.8 kg/25 mm were confirmed to have "peeling" of 2% (2 patches) at 9 months and 8% (8 patches) at 12 months. These results demonstrated that a heat seal strength of at least 1.0 kg/25 mm can adequately prevent peeling of heat seal sections during storage periods.

INDUSTRIAL APPLICABILITY

As explained above, the present invention provides a patch package which sufficiently reduces the effect of moisture on the drug in a patch and can stably hold the patch for prolonged periods, while also having excellent economy and handleability. The invention also employs this patch package to realize a packaged patch that can satisfactorily maintain the releasability of a drug in the patch.

What is claimed is:

1. A patch package adapted for receiving a pharmaceutical patch comprising:
   (a) a first sheet consisting of:
      a first moisture-permeable material layer comprising a first resin and having a moisture permeability of 40–120 g/m²/day;
      a first screen material layer that is comprised of two layers for blocking penetration of moisture and light; and
      a first hygroscopic material layer located between the first moisture-permeable material layer and the first screen material layer and comprising a first resin containing 20–40 wt % of inorganic filler; and
   (b) a second sheet consisting of:
      a second moisture-permeable material layer comprising a second resin and having a moisture permeability of 40–120 g/m²/day, the second moisture-permeable layer facing the first moisture-permeable material layer;
      a second screen material layer that is comprised of two layers for blocking penetration of moisture and light; and
      a second hygroscopic material layer located between the second moisture-permeable material layer and the second screen material layer and comprising a second resin containing 20–40 wt % of inorganic filler;
   wherein the first moisture-permeable layer and the second moisture-permeable layer being directly in contact with each other at peripheral areas thereof and fixed to each other at the peripheral areas by heat sealing to form a package shape, and
   at the peripheral areas, the first hygroscopic material layer and the second hygroscopic material layer are located, respectively, between the first moisture-permeable material layer and the first screen material layer, and between the second moisture-permeable material layer and the second screen material layer.

2. A patch package according to claim 1, wherein said first resin and the second resin are low density polyethylene, and the two layers that form the screen material layer are a metal foil layer and a high density polyethylene layer.

3. A patch package according to claim 2, wherein the thickness of the hygroscopic material layer is 20–40 μm, the thickness of the moisture-permeable material layer is 5–15 μm, the thickness of the high-density polyethylene layer composing the screen material layer is 10–30 μm and the thickness of the metal foil composing the screen material layer is 5–15 μm.

4. A patch package according to claim 1, wherein the heat seal strength is from 1.0 kg/25 mm to 5.0 kg/25 mm.

5. A packaged patch comprising:
   a patch having a support and a pressure-sensitive adhesive laminated on the support;
   a patch package comprising;
      (a) a first sheet consisting of:
         a first moisture-permeable material layer comprising a first resin and having a moisture permeability of 40–120 g/m²/day;
         a screen material layer that is comprised of two layers for blocking penetration of moisture and light; and
         a first hygroscopic material layer located between the first moisture-permeable material layer and the first screen material layer and comprising a first resin containing 20–40 wt % of inorganic filler; and
      (b) a second sheet consisting of:
         a second moisture-permeable material layer comprising a second resin and having a moisture permeability of 40–120 g/m²/day, the second moisture-permeable layer facing the first moisture-permeable material layer;
         a second screen material layer that is comprised of two layers for blocking penetration of moisture and light; and
         a second hygroscopic material layer located between the second moisture-permeable material layer and the second screen material layer and comprising a second resin containing 20–40 wt % of inorganic filler;
   the first moisture-permeable layer and the second moisture-permeable layer being directly in contact with each other at peripheral areas thereof and fixed to each other at the peripheral areas by heat sealing to form a package shape,
   wherein the pressure-sensitive adhesive is composed mainly of a styrene-isoprene-styrene blocked copolymer, wherein the total surface area of the interior of the patch package is 1.2–10 times the effective area of said patch, and wherein said patch is in said package, and
   at the peripheral areas, the first hygroscopic material layer and the second hygroscopic material layer are located, respectively, between the first moisture-permeable material layer and the first screen material layer, and between the second moisture-permeable material layer and the second screen material layer.

6. A patch package adapted and configured to receive a pharmaceutical patch comprising a first sheet and a second sheet, wherein each sheet consists of:
   (a) a first layer being a moisture-permeable material layer, said first layer comprising a first resin and having a moisture permeability of 40–120 g/m²/day;
   (b) a second layer being a hygroscopic material layer that comprises a second resin containing 20–40 wt % of inorganic filler; and
   (c) a third layer and a fourth layer forming a screen material layer for blocking penetration of moisture and light,
   wherein the moisture-permeable layers of said first sheet and said second sheet being directly in contact with each other at peripheral areas thereof and fixed to each other at the peripheral areas by heat sealing so as to form a package shape, and
   at the peripheral areas, the respective hygroscopic material layers of said first sheet and said second sheet are located between the respective moisture-permeable material layers and screen material layers of the respective sheets.

7. A packaged patch comprising a pharmaceutical patch having a support and a pressure-sensitive adhesive laminated on the support within a patch package that comprises a first sheet and a second sheet, wherein each sheet consists of:
   (a) a first layer being a moisture-permeable material layer, said first layer comprising a first resin and having a moisture permeability of 40–120 g/m²/day;
   (b) a second layer being a hygroscopic material layer that comprises a second resin containing 20–40 wt % of inorganic filler; and (c) a third layer and a fourth layer forming a screen material layer for blocking penetration of moisture and light, wherein the moisture-permeable layers of said first sheet and said second sheet being directly in contact with each other at peripheral areas thereof and fixed to each other at the peripheral areas by heat sealing so as to form a package shape, wherein the total surface area of the interior of the patch package is 1.2–10 times the effective area of said patch, and at the peripheral areas, the respective hygroscopic material layers of said first sheet and said second sheet are located between the respective moisture-permeable material layers and screen material layers of the respective sheets.

8. A packaged patch according to claim 7, wherein the pressure sensitive adhesive is compound mainly of a styrene blocked copolymer.

9. A packaged patch according to claim 7, wherein said pharmaceutical patch contains eperisone, estradiol or its derivatives, dantrolene, diclofenac sodium or scopolamine.

10. A packaged patch according to claim 7, wherein said pharmaceutical patch contains at least one drug selected from the group consisting of antiemetics, polakisuria agents, Ca antagonists, corticosteroids, anti-inflammatory analgesics, hypnotic analgesics, neuoleptics, antihypertensive agents, hypotensive diuretics, antibiotics, antibacterial agents, vitamins, antitussives, antidepressants, cerebral circulation ameiorants, anticancer agents, muscle relaxants, analgesics, immunoregulators, choleretic agents, smoking cessation aides, agents for diabetics, gout treatment agents, antiparkinson agents, antivertigo agents and antispasmodics.

11. A patch package according to claim 1, wherein the pharmaceutical patch contains at least one drug selected from the group consisting of antiemetics, polakisuria agents, Ca antagonists, corticosteroids, anti-inflammatory analgesics, hypnotic analgesics, neuoleptics, antihypertensive agents, hypotensive diuretics, antibiotics, antibacterial agents, vitamins, antitussives, antidepressants, cerebral circulation ameiorants, anticancer agents, muscle relaxants, analgesics, immunoregulators, choleretic agents, smoking cessation aides, agents for diabetics, gout treatment agents, antiparkinson agents, antivertigo agents and antispasmodics.

12. A packaged patch according to claim 6, wherein the pharmaceutical patch contains at least one drug selected from the group consisting of antiemetics, polakisuria agents, Ca antagonists, corticosteroids, anti-inflammatory analgesics, hypnotic analgesics, neuoleptics, antihypertensive agents, hypotensive diuretics, antibiotics, antibacterial agents, vitamins, antitussives, antidepressants, cerebral circulation ameiorants, anticancer agents, muscle relaxants, analgesics, immunoregulators, choleretic agents, smoking cessation aides, agents for diabetics, gout treatment agents, antiparkinson agents, antivertigo agents and antispasmodics.

13. A patch package adapted for receiving a pharmaceutical patch comprising:

(a) a first sheet consisting of:

a first moisture-permeable material layer comprising a first resin and having a moisture permeability of 40–120 g/m$^2$/day;

a first screen material layer that is comprised of two layers for blocking penetration of moisture and light; and a first hygroscopic material layer located between the first moisture-permeable material layer and the first screen material layer and comprising a first resin containing 20–40 wt % of inorganic filler; and (b) a second sheet consisting of:

a second moisture-permeable material layer comprising a second resin and having a moisture permeability of 40–120 g/m$^2$/day, the second moisture-permeable layer facing the first moisture-permeable material layer;

a second screen material layer that is comprised of two layers for blocking penetration of moisture and light; and a second hygroscopic material layer located between the second moisture-permeable material layer and the second screen material layer and comprising a second resin containing 20–40 wt % of inorganic filler;

wherein the first moisture-permeable layer and the second moisture-permeable layer being directly in contact with each other at peripheral areas thereof and sealed to each other at the peripheral areas to form a package shape, and at the peripheral areas, the first hygroscopic material layer and the second hygroscopic material layer are located, respectively, between the first moisture-permeable material layer and the first screen material layer, and between the second moisture-permeable material layer and the second screen material layer.

14. A patch package according to claim 13, wherein the first moisture-permeable layer and the second moisture-permeable layer are sealed to each other by heat sealing at the peripheral areas thereof.

15. A patch package according to claim 13, wherein the pharmaceutical patch contains at least one drug selected from the group consisting of antiemetics, polakisuria agents, Ca antagonists, corticosteroids, anti-inflammatory analgesics, hypnotic analgesics, neuoleptics, antihypertensive agents, hypotensive diuretics, antibiotics, antibacterial agents, vitamins, antitussives, antidepressants, cerebral circulation ameiorants, anticancer agents, muscle relaxants, analgesics, immunoregulators, choleretic agents, smoking cessation aides, agents for diabetics, gout treatment agents, antiparkinson agents, antivertigo agents and antispasmodics.

* * * * *